United States Patent [19]

Nachbur et al.

[11] 4,026,889
[45] May 31, 1977

[54] PHOSPHORUS-CONTAINING CONDENSATION PRODUCTS

[75] Inventors: Hermann Nachbur, Dornach; Arthur Maeder, Therwil, both of Switzerland

[73] Assignee: Ciba-Geigy Corporation, Ardsley, N.Y.

[22] Filed: Oct. 21, 1975

[21] Appl. No.: 624,630

Related U.S. Application Data

[63] Continuation of Ser. No. 285,169, Aug. 31, 1972, abandoned.

[52] U.S. Cl. .......................... 260/249.9; 252/8.1; 106/15 FP
[51] Int. Cl.² .................................... C07D 251/72
[58] Field of Search ................................ 260/249.9

[56] References Cited

UNITED STATES PATENTS

| | | | |
|---|---|---|---|
| 2,668,096 | 2/1954 | Reeves et al. ...................... | 8/115.5 |
| 2,772,188 | 11/1956 | Reeves et al. ...................... | 117/136 |
| 2,809,941 | 10/1957 | Reeves et al. ...................... | 260/2 |
| 2,911,322 | 11/1959 | Klein et al. ........................ | 117/76 |
| 2,983,623 | 5/1961 | Coates ................................ | 117/62 |
| 2,993,746 | 7/1961 | Miles et al. ....................... | 8/116 |
| 3,421,923 | 1/1969 | Guth ................................. | 117/62.2 |
| 3,551,422 | 12/1970 | Tesoro et al. ..................... | 260/249.8 |
| 3,634,422 | 1/1972 | Nachbur et al. ................... | 260/249.8 |
| 3,654,274 | 4/1972 | Chance et al. ..................... | 260/249.8 |

FOREIGN PATENTS OR APPLICATIONS

| | | |
|---|---|---|
| 211,637 | 10/1955 | Australia |
| 1,419,478 | 2/1969 | Germany |
| 1,221,605 | 7/1966 | Germany |
| 1,294,340 | 5/1969 | Germany |
| 1,419,474 | 10/1969 | Germany |
| 1,419,477 | 2/1970 | Germany |
| 740,269 | 11/1955 | United Kingdom |
| 761,985 | 11/1956 | United Kingdom |
| 784,318 | 10/1957 | United Kingdom |
| 800,157 | 8/1958 | United Kingdom |
| 882,993 | 11/1961 | United Kingdom |
| 884,785 | 12/1961 | United Kingdom |
| 938,990 | 10/1963 | United Kingdom |
| 1,126,432 | 9/1968 | United Kingdom |

OTHER PUBLICATIONS

John D. Guthrie et al.; American Dyestuff Reporter vol. 44, pp. 328–332 (May 1955).
A. J. Hall, "Textile Finishing", pp. 394–396 (1966) Heywood Books.

*Primary Examiner*—John M. Ford
*Attorney, Agent, or Firm*—Karl F. Jorda; Edward McC. Roberts; Prabodh I. Almaula

[57] ABSTRACT

The subject of the invention is a process for the manufacture of water-soluble condensation products of hydroxymethylphosphonium compounds and bicyclic dienes, characterized in that (a) one mol of a tetrakis-(hydroxymethyl)-phosphonium compound is condensed with (b) 0.02 to 1 mol, preferably 0.1 to 0.5 mol, of a 2,4,6,8,9-pentaazo-bicyclo-[3.3.1]-nona-2,6-diene of the formula

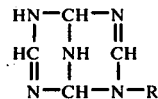

(1)

or its salt, wherein R represents hydrogen, hydroxyl or an optionally substituted aliphatic, cycloaliphatic, aromatic or heterocyclic radical; at 40° to 120° C, optionally in the presence of formaldehyde or a formaldehyde-releasing agent and optionally in the presence of an inert organic solvent, the condensation is optionally thereafter continued at temperatures of 100° to 150° C and, if appropriate, free hydroxyl groups are etherified at least partially with at least one alkanol with 1 to 4 carbon atoms and, if appropriate, the salts of the condensation products are converted into the corresponding hydroxides.

The condensation products are used for flameproofing organic fiber material, especially textiles.

10 Claims, No Drawings

PHOSPHORUS-CONTAINING CONDENSATION PRODUCTS

This is a continuation of application Ser. No. 285,169, filed on Aug. 31, 1972, now abandoned.

The subject of the invention is a process for the manufacture of water-soluble condensation products of hydroxymethylphosphonium compounds and bicyclic dienes, characterised in that (a) one mol of a tetrakis-(hydroxymethyl)-phosphonium compound is condensed with (b) 0.02 to 1 mol, preferably 0.1 to 0.5 mol, of a 2,4,6,8,9-pentaazo-bicyclo-[3.3.1]-nona-2,6-diene of the formula

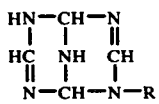
(1)

or its salt, wherein R represents hydrogen, hydroxyl or an optionally substituted aliphatic, cycloaliphatic, aromatic or heterocyclic radical; at 40° to 120° C, optionally in the presence of formaldehyde or a formaldehyde-releasing agent and optionally in the presence of an inert organic solvent, the condensation is optionally thereafter continued at temperatures of 100° to 150° C and, if appropriate, free hydroxyl groups are etherified at least partially with at least one alkanol with 1 to 4 carbon atoms and, if appropriate, the salts of the condensation products are converted into the corresponding hydroxides.

The condensation is preferably carried out at 70° to 110° C in an inert organic solvent or solvent mixture. For this, aromatic hydrocarbons are above all suitable, such as, for example, toluene, o-, m- or p-xylene or a mixture thereof, or xylene-toluene, xylene-benzene or xylene-decahydronaphthalene mixtures. Preferably, the optional subsequent further condensation is carried out at 125° to 140° C, in particular, at about 135° C, that is to say the boiling point of the solvent mixture.

At the same time it is, however, also possible to carry out the condensation in the absence of an inert organic solvent, for example by using already prepared condensation product as the solvent or by carrying out the condensation in the melt.

An appropriate procedure is to heat the tetrakis-(hydroxymethyl)-phosphonium compound, which as a rule is in the form of an aqueous solution, together with the component (b), optionally in a solvent, to the boil and to distil off the water. Possible tetrakis-(hydroxymethyl)-phosphonium compounds are above all salts and the hydroxide.

Amongst the tetrakis-(hydroxymethyl)-phosphonium salts used, the halides, such as, for example, the bromide or especially the chloride are preferred. Tetrakis-(hydroxymethyl)phosphonium chloride is hereafter referred to as THPC.

Where the tetrakis-(hydroxymethyl)phosphonium hydroxide (THPOH) is used as the starting product, it is appropriately manufactured beforehand from a corresponding salt, for example THPC, by neutralisation, in aqueous solution, with a base, for example sodium hydroxide, followed by dehydration.

The component (b) is preferably a component of the formula

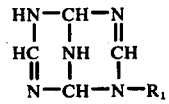
(2)

wherein $R_1$ denotes hydrogen, hydroxyl, alkyl, alkenyl, cycloalkyl, hydroxyalkyl, dialkylaminoalkyl, phenyl, hydroxyphenyl, N-morpholyl-alkyl, pyridyl, pyrimidyl or piperazine-alkyl.

Alkyl and alkenyl radicals in R or $R_1$ are, as a rule, lower alkyl and alkenyl radicals, that is to say preferably contain at most 4 carbon atoms, especially 1 or 2, for example methyl.

Compounds of the formula

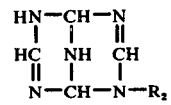

wherein $R_2$ denotes alkyl with 1 or 2 carbon atoms or hydroxyalkyl with 1 or 2 carbon atoms or above all hydrogen, are particularly advantageous.

The radical R—N<, or $R_1$—N<, or $R_2$—N< in the compounds of the formulae (1) to (3) is derived, for example, from the following monoamines: ammonia, methylamine, ethylamine, ethanolamine, hydroxylamine, allylamine, n-propylamine, n-butylamine, isobutylamine, amylamine, stearylamine, oleylamine, cyclohexylamine, diethylaminoethylamine, aniline, p-aminophenol, aminopropylmorpholine, aminoethylpiperazine, aminopyrimidine or aminopyridine. The compounds of the formula (1) can in particular also be employed in the form of their water-soluble salts, for example as salts of organic acids, alkylcarboxylic aicds with 1 to 3 carbon atoms, such as formic acid or acetic acid, or, preferably, as salts of inorganic acids, such as phosphoric acid, hydrochloric acid or sulphuric acid.

The compounds of the formula (1) are known, for example from U.S. Pat. No. 3,290,310. They are obtained, for example, by reaction of the salt of the corresponding amine with dicyandiamide and formaldehyde.

The formaldehyde which is optionally used conjointly in the manufacture of the phosphorus—containing condensation products is preferably in the form of an aqueous solution. Possible formaldehyde-releasing agents are above all paraformaldehyde.

The etherification, which is optionally to be carried out, of the condensation product which still contains free hydroxyl groups is effected with, for example, n-butanol, n-propanol, ethanol or especially methanol. Preferably, this is done in an acid medium.

The acid catalysts optionally used conjointly in the condensation are preferably acid salts (Lewis acids) such as magnesium chloride, iron-III chloride, zinc nitrate or boron trifluoride/diethyl ether. The conjoint use of these catalysts is particularly advisable in the case of the condensation with THPOH.

After completion of condensation and if appropriate, etherification, the salts of the condensation products can also be completely or partially converted into their corresponding hydroxides, which as a rule is achieved by adding strong bases, such as alkali metal hydroxides or alkaline earth metal hydroxides, for example sodium hydroxide potassium hydroxide or calcium hydroxide, and also sodium carbonate. The amount of base is appropriately so chosen that the pH value of the reaction mixture is about 5 to 8. This conversion is appropriately effected in the application bath.

At times, the end products have an unpleasant odour caused by volatile low molecular trivalent phosphorus compounds, for example phosphines, such as trihydroxymethylphosphine. This odour can be eliminated by an oxidative after-treatment of the condensation product, for example by passing air or oxygen into the reaction mixture or by adding oxidising agents, such as hydrogen peroxide or potassium persulphate.

The condensation products are used for flameproofing organic fibre material, especially textiles. An appropriate procedure for this is to treat these materials with an aqueous preparation which contains at least (1) a condensation product of the indicated nature and (2) a polyfunctional compound which differs from the condensation products according to (1) and to finish the materials treated in this way by the wet batch process, above all by the moist batch process, or ammonia process, or especially by the thermofixing process.

The component (2) preferably consists of polyfunctional nitrogen compounds. Possible epoxides are above all epoxides which are liquid at room temperature and have at least two epoxides groups which are preferably derived from polyhydric phenols. Polyfunctional nitrogen compounds are, for example, polyalkylenepolyamines or, in particular, aminoplast-forming agents or aminoplast precondensates. The latter are preferred.

By aminoplast-forming agents there are understood nitrogen compounds which can be methylolated, and by aminoplast precondensates there are understood addition products of formaldehyde to nitrogen compounds which can be methylolated. As aminoplast-forming agents or nitrogen compounds which can be methylolated, there may be mentioned: 1,3,5-aminotriazines such as N-substituted melamines, for example N-butylmelamine, N-trihalogenomethylmelamines, triazones, and also ammeline, guanimines, for example benzoguanamines or acetoguanamines, or also diguanamines.

Further possibilities are: cyanamide, acrylamide, alkylurea or arylurea and alkylthioureas or arylthioureas, alkyleneureas or alkylenediureas, for example urea, thiourea, urones, ethyleneurea, propyleneurea, acetylenediurea or especially 4,5-dihydroxyimidazolidone-2 and derivatives thereof, for example 4,5-dihydroxyimidazolidone-2 substituted in the 4-position, at the hydroxyl group, by the $-CH_2CH_2CO-NH-CH_2OH$ radical. The methylol compounds of a urea of an ethyleneurea or especially of melamine are preferentially used. Valuable products are provided in general by products which are as highly methylolated as possible, but in particular also be products with low methylolation, for example methylolated melamines such as di- or trimethylolmelamine or mixtures thereof. Suitable aminoplast procondensates are both predominantly monomolecular aminoplasts and also more highly precondensed aminoplasts.

The ethers of these aminoplast precondensates can also be used together with the reaction products. For example, the ethers of alkanols such as methanol, ethanol, n-propanol, isopropanol, n-butanol or pentanols, are of advantage. It is however desirable that these aminoplast precondensates should be water-soluble, such as, for example, the pentamethylolmelamine-dimethyl-ether or trimethylolmelamine-dimethylether.

The organic fibre materials to be provided with a flameproof finish are, for example, wood, paper, furs, hides or, preferably, textiles. In particular, fibre materials of polyamides, cellulose, cellulose-polyester or polyester are flameproofed with fabrics of wool or polyester or above all mixed fabrics of polyester and cellulose, wherein the ratio of the polyester constituent to the cellulose constituent is 1:4 to 2:1, being preferred. Thus, for example, so-called 20/80, 26/74, 50/50 or 67/33 polyester-cellulose mixed fabrics can be used.

The cellulose or the cellulose constituent of the fibre material originates, for example, from linen, cotton, rayon or staple viscose. In addition to polyester-cellulose fibre mixtures it is also possible to use fibre mixtures of cellulose with natural or synthetic polyamides. Above all, fibre materials of wood can also be flameproofed well with the polycondensation products.

The aqueous preparations for flameproofing the organic fibre materials as a rule contain 200 to 800 g/l, preferably 350 to 650 g/l, of the component (1) and 20 to 200 g/l, preferably 40 to 120 g/l, of the component (2). The preparations in most cases have an acid to neutral or weakly alkaline pH value.

The preparations for flameproofing can optionally contain yet further additives. To achieve a greater deposit of material on fabrics it is advantageous, for example, to add 0.1 to 0.5% of a high molecular polyethylene glycol. Further, the customary plasticisers, for example an aqueous polyethylene emulsion or silicone oil emulsion, can be added to the preparations.

To improve the mechanical strengths of the fibres, suitable copolymers can also be added to the preparations, for example copolymers of N-methylolacrylamide or cationic copolymers. For example, aqueous emulsions of copolymers of (a) 0.25 to 10% of an alkaline earth metal salt of an $\alpha,\beta$-ethylenically unsaturated monocarboxylic acid, (b) 0.25 to 30% of a N-methylolamide or N-methylolamide-ether of an $\alpha,\beta$-ethylenically unsaturated monocarboxylic or dicarboxylic acid and (c) 99.5 to 60% of at least one other copolymerisable compound are advantageous in this context. These copolymers and ther manufacture are known. The tenacity and abrasion resistance of the treated fibre material can be favourably influenced by the conjoint use of such a copolymer.

If a polymer of the indicated type is further added to the preparation, the amounts are advantageously small, for example 1 to 10%, relative to the amount of the condensation product. The same is true of any plasticiser, where the appropriate amounts can again be 1 to 10%.

It is also possible, though in most cases not necessary, to add curing catalysts such as, for example, ammonium chloride, ammonium dihydrogen orthophosphate, phosphoric acid, magnesium chloride or zinc nitrate.

The pH value of the preparations is as a rule 2 to 7.5, preferably 4 to 7, and is adjusted in the usual manner by adding bases and acids.

It can also be advantageous to add buffer substances, for example $NaHCO_3$, disodium phosphate and trisodium phosphate and triethanolamine.

To improve the durability of the flameproof finishes and to achieve a soft handle, it can be advantageous to add to the aqueous preparations halogenated paraffins in combination with a polyvinyl halide compound.

The preparations are now applied to the fibre materials, and this can be done in a manner which is in itself known. Preferably, piece goods are used and impregnated on a padder which is charged with the preparation at room temperature.

In the preferred thermofixing process, the fibre material impregnated in this way must now be dried and subjected to a heat treatment. It is appropriately dried at temperatures of up to 100° C. Thereafter the material is subjected to a heat treatment at temperatures above 100° C, for example 100° to 200° C, preferably 120° to 180° C, the duration of which can be the shorter, the higher is the temperature. This duration of heating, is, for example, 30 seconds to 10 minutes.

If the moist fixing process is used, the fabric is first dried to a residual moisture content of about 5 to 20% and then batched for 12 to 48 hours at about 40° to 60° C, rinsed, washed and dried. In the wet fixing process, a similar procedure is followed except that the completely wet fibre material is batched. In the ammonia fixing process, the treated fibre material is first, in the moist state, gassed with ammonia and is subsequently dried.

A rinse with an acid-binding agent, preferably with aqueous sodium carbonate solution, can be desirable in the case of a strongly acid reaction medium.

The percentages and parts in the examples which follow are parts by weight or percentages by weight. The relationship of parts by volume to parts by weight is as of ml to g.

EXAMPLE 1

244 parts of a 78% strength aqueous solution of THPC (1 mol) and 203 parts (0.5 mol) of a 40% strength aqueous solution of a compound of the formula

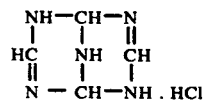

(4)

are treated for 2 hours at 100° C internal temperature in a stirred vessel of 500 parts by volume capacity, which is equipped with a thermometer and reflux condenser. Thereafter the solution is concentrated in vacuo at 60° C to 80% active substance content.

307 parts of a solution of low viscosity are obtained. The active substance content is 81.5%. The infrared spectrum of this product shows the following bands:

| | | | | |
|---|---|---|---|---|
| Broad shoulder | band at approx. | 3,240 cm⁻¹ | strong |
| Broad shoulder | " | 2,920 | " | weak |
| Broad shoulder | " | 2,850 | " | medium |
| Broad shoulder | " | 2,650 | " | medium |
| Broad shoulder | " | 2,480 | " | weak-medium |
| Broad shoulder | " | 2,360 | " | weak-medium |
| Broad | " | 2,080 | " | weak-medium |
| Broad shoulder | " | 1,700 | " | strong |
| Broad | " | 1,635 | " | weak |
| Broad shoulder | " | 1,535 | " | weak |
| Broad shoulder | " | 1,500 | " | weak |
| Broad shoulder | " | 1,400 | " | weak |
| Broad shoulder | " | 1,300 | " | weak |
| Broad shoulder | " | 1,270 | " | weak |
| Broad shoulder | " | 1,190 | " | weak |
| Broad shoulder | " | 1,115 | " | weak |
| Broad | " | 1,045 | " | medium |
| Broad shoulder | " | 910 | " | medium |
| Broad shoulder | " | 880 | " | weak |
| Broad shoulder | " | 810 | " | weak |

EXAMPLE 2

244 parts (1 mol) of a 78% strength aqueous THPC solution and 145 parts (0.5 mol) of a 66% strength aqueous solution of a compound of the formula

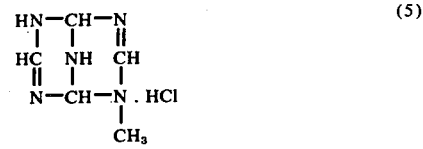

(5)

are condensed for 2 hours at 100° – 105° C in a stirred vessel of 500 parts by volume capacity equipped with a reflux condenser and thermometer. After cooling, 388 parts of a yellowish-coloured aqueous solution of the condensation product are obtained. The phosphorus content of this solution is 8%. The infrared spectrum of this product shows the following bands:

| | | | | |
|---|---|---|---|---|
| Broad | band at approx. | 3,240 cm⁻¹ | strong |
| Broad shoulder | " | 2,920 | " | weak |
| Broad shoulder | " | 2,850 | " | medium |
| Broad shoulder | " | 2,650 | " | medium |
| Broad shoulder | " | 2,470 | " | weak |
| Broad shoulder | " | 2,360 | " | weak |
| Broad | " | 2,080 | " | weak |
| Sharp shoulder | " | 1,725 | " | medium-strong |
| Broad | " | 1,625 | " | medium-strong |
| Broad | " | 1,510 | " | weak |
| Broad shoulder | " | 1,410 | " | weak |
| Broad shoulder | " | 1,390 | " | weak |
| Broad | " | 1,300 | " | weak |
| Broad | " | 1,200 | " | weak |
| Broad shoulder | " | 1,165 | " | weak |
| Broad shoulder | " | 1,105 | " | weak |
| Broad | " | 1,040 | " | medium-strong |
| Broad shoulder | " | 910 | " | medium |
| Broad shoulder | " | 880 | " | weak-medium |
| Broad shoulder | " | 810 | " | weak |

EXAMPLE 3

244 parts (1 mol) of a 78% strength aqueous THPC solution, 21.2 parts of a 35.4% strength aqueous formaldehyde solution (0.25 mol) and 101.5 parts of a 40% strength aqueous solution of a compound of the formula (4) are condensed for 2 hours at 100° – 105° C in a stirred vessel of 500 parts by volume capacity which is equipped with a reflux condenser and thermometer. After cooling, 363 parts of a colourless aqueous solution of the condensation product are obtained. The phosphorus content is 8.55%. The infrared spectrum of this product shows the following bands:

| | | | | |
|---|---|---|---|---|
| Broad | band at approx. | 3,240 cm⁻¹ | strong |
| Broad shoulder | " | 2,930 | " | weak |
| Broad shoulder | " | 2,850 | " | medium |
| Broad shoulder | " | 2,650 | " | weak-medium |
| Broad shoulder | " | 2,470 | " | weak |
| Broad shoulder | " | 2,360 | " | weak |
| Broad | " | 2,080 | " | weak-medium |
| Sharp shoulder | " | 1,730 | " | medium-strong |
| Broad | " | 1,630 | " | medium-strong |
| Broad | " | 1,515 | " | weak |
| Broad shoulder | " | 1,415 | " | weak |
| Broad shoulder | " | 1,390 | " | weak |
| Broad | " | 1,310 | " | weak |
| Broad | " | 1,200 | " | weak |
| Broad shoulder | " | 1,170 | " | weak |
| Broad shoulder | " | 1,110 | " | weak |
| Broad | " | 1,045 | " | medium-strong |
| Broad shoulder | " | 915 | " | medium |
| Broad shoulder | " | 885 | " | weak-medium |
| Broad shoulder | " | 815 | " | weak |

EXAMPLE 4

105 parts (approx. 0.25 mol) of a 40% strength aqueous solution of a compound of the formula (4) and 200 parts of xylene isomer mixture are warmed to the boil in a stirred vessel of 500 parts by volume capacity which is equipped with a water separator, reflux condenser and thermometer. Whilst doing so, 59 parts of water are removed azeotropically. Thereafter 244 parts of a 78% strength aqueous THPC solution (1 mol) are added and the azeotropic removal of water is continued until a total of 136 parts of water have been separated off. Towards the end of the condensation reaction the boiling point reaches 130° C. The mixture is now cooled to 100° C and the condensation product is again dissolved by adding 200 parts of water. The xylene is siphoned off as far as possible and the aqueous solution is again freed of the water and of residual amounts of xylene in vacuo at 70° C. 188 parts of a highly viscous product is obtained and is diluted with water to 80% active substance content to facilitate handling. The phosphorus content of this solution is 13.2%. The infrared spectrum shows the following bands:

| Broad | band at approx. | 3,240 | cm$^{-1}$ | strong |
|---|---|---|---|---|
| Sharp shoulder | " | 2,920 | " | weak |
| Broad shoulder | " | 2,850 | " | weak-medium |
| Broad shoulder | " | 2,640 | " | weak-medium |
| Broad shoulder | " | 2,460 | " | weak |
| Broad shoulder | " | 2,350 | " | weak |
| Broad | " | 2,080 | " | weak |
| Broad shoulder | " | 1,700 | " | medium-strong |
| Broad | " | 1,625 | " | medium-strong |
| Broad | " | 1,510 | " | weak-medium |
| Broad | " | 1,410 | " | weak-medium |
| Broad | " | 1,295 | " | weak-medium |
| Broad shoulder | " | 1,200 | " | weak |
| Sharp shoulder | " | 1,160 | " | weak-medium |
| Broad shoulder | " | 1,110 | " | weak |
| Sharp | " | 1,040 | " | strong |
| Broad | " | 910 | " | medium |
| Broad | " | 880 | " | weak-medium |
| Broad shoulder | " | 810 | " | weak |

EXAMPLE 5

244 parts (1 mol) of a 78% strength aqueous THPC solution are cooled to 10° C in a stirred vessel of 1,000 parts by volume capacity, which is equipped with a reflux condenser and thermometer, and are neutralised to pH 7.2 with 58.6 parts of 30% strength aqueous sodium hydroxide solution whilst stirring rapidly and cooling with ice. Thereafter, 406 parts of a 40% strength aqueous solution (1 mol) of a compound of the formula (4) are added and condensation is carried out for 30 minutes at 80° C internal temperature. Thereafter the water is removed in vacuo to the point that after cooling a viscous condensate, which can still be poured, remains. Yield: 414 parts. The phosphorus content of this product is 7.5%. The infrared spectrum of this product shows the following bands:

| Broad | band at approx. | 3,240 | cm$^{-1}$ | strong |
|---|---|---|---|---|
| Broad shoulder | " | 2,920 | " | weak |
| Broad shoulder | " | 2,850 | " | medium |
| Broad shoulder | " | 2,650 | " | weak-medium |
| Broad shoulder | " | 2,480 | " | weak |
| Broad shoulder | " | 2,360 | " | weak |
| Sharp | " | 2,180 | " | weak-medium |
| Broad shoulder | " | 2,080 | " | weak-medium |
| Broad shoulder | " | 1,710 | " | strong |
| Broad shoulder | " | 1,620 | " | medium |
| Broad shoulder | " | 1,520 | " | weak |
| Broad shoulder | " | 1,390 | " | weak |
| Broad | " | 1,315 | " | weak |
| Broad | " | 1,175 | " | weak |
| Broad shoulder | " | 1,115 | " | weak |
| Broad | " | 1,045 | " | medium-strong |
| Broad shoulder | " | 915 | " | medium |
| Broad shoulder | " | 885 | " | weak |
| Broad shoulder | " | 805 | " | weak |

EXAMPLE 6

190.5 parts (1 mol) of anhydrous crystalline THPC and 3.25 parts (0.02 mol) of a compound of the formula (4) are condensed for 2 hours in the melt, at 100° – 105° C internal temperature, in a stirred vessel of 500 parts by volume capacity which is equipped with a reflux condenser and thermometer. Thereafter the mixture is cooled to 50° C, 80 parts of methanol and 0.1 part of 37% strength aqueous hydrochloric acid are added and etherification is carried out for 30 minutes at the reflux temperature (approx. 64° C). The excess methanol is finally removed in vacuo. 188 parts of a reddish-coloured waxy condensation product are obtained. The phosphorus content is 16.5%. The infrared spectrum of this product shows the following bands:

| Broad | band at approx. | 3,240 | cm$^{-1}$ | strong |
|---|---|---|---|---|
| Sharp | " | 2,920 | " | weak |
| Broad shoulder | " | 2,850 | " | medium |
| Broad shoulder | " | 2,640 | " | weak-medium |
| Broad shoulder | " | 2,480 | " | weak |
| Broad shoulder | " | 2,360 | " | weak |
| Sharp | " | 2,070 | " | weak |
| Broad shoulder | " | 1,710 | " | weak |
| Broad | " | 1,635 | " | medium |
| Broad | " | 1,415 | " | medium |
| Sharp | " | 1,300 | " | weak |
| Broad | " | 1,200 | " | weak |
| Broad shoulder | " | 1,165 | " | weak |
| Broad shoulder | " | 1,105 | " | weak |
| Sharp | " | 1,045 | " | strong |
| Sharp shoulder | " | 920 | " | medium |
| Broad shoulder | " | 875 | " | weak-medium |
| Broad | " | 815 | " | weak |

EXAMPLE 7

Mixed fabrics of polyester-cotton (PES/CO), 50:50 and 67:33, are padded with the liquors according to Table 1 below, dried for 30 minutes at about 80° C and subsequently cured for 5 minutes at 150° C.

The fabric is then washed for 5 minutes at 60° C in a liquor which per liter contains 5 ml of hydrogen peroxide (35% strength), 3 g of sodium hydroxide solution (30% strength) and 1 g of a 25% strength aqueous solution of a condensation product of 1 mol of p-tert.-nonylphenol and 9 mols of ethylene oxide Thereafter it is rinsed and dried. The degree of fixing indicates the amount of the product present on the fibre material after rinsing (relative to the amount originally taken up).

The fabrics are then washed up to 40 times for 45 minutes at 60° C in a domestic washing machine, using a liquor which contains 4 g/l of a domestic detergent (SNV 198,861 wash). The individual fabric samples are then tested for their flameproof character (DIN 53,906 vertical test; ignition time 6 seconds).

The results are summarised in Table 1 below.

Table 1

| Constituents g/l | Treated with liquors PES:CO 67:33 | PES:CO 50:50 |
|---|---|---|
| Product according to Example 1 | 710. | 710 |
| Dimethylolmelamine | 96.5 | 96.5 |
| pH value of the liquor (adjusted with NaOH) | 5.8 | 5.8 |
| g of phosphorus per kg of fabric | 52 | 52 |
| Liquor uptake, % | 75 | 75 |
| Degree of fixing, % | 70 | 66 |
| Flameproof character | | |
| After rinsing | | |
| Smouldering time (seconds) | 0 | 0 |
| Tear length (cm) | 10.5 | 8.5 |
| After 20 washes | | |
| Smouldering time (seconds) | 0 | 0 |
| Tear length (cm) | 9 | 7.5 |
| After 40 washes | | |
| Smouldering time (seconds) | 0 | 0 |
| Tear length (cm) | 9.5 | 7 |

Untreated fabric burns in all the tests of flameproof character.

EXAMPLE 8

Fabrics of polyester/cotton, PES/CO, 67:33 and 50:50, are padded with the liquors of Table 3 below and then aftertreated as follows:

a. By the moist fixing or moist batch process: after padding batch at 10% residual moisture content for 24 hours at 50° C, thereafter rinse with cold water and wash for 5 minutes in a bath which contains 4 g/l of sodium carbonate and 1 g/l of a condensation product of 1 mol of p-tert.-nonylphenol and 9 mols of ethylene oxide, then rinse and dry.

b. By the wet fixing or wet batch process: after padding batch wet for 24 hours at 50° C and subsequently rinse and wash as under a). The fabrics are then tested for their flameproof character according to DIN 53,906 (ignition time 6 seconds). Untreated fabrics burn away.

The results are summarised in Table 2 below.

Table 2

| | Fabrics treated with | | | |
|---|---|---|---|---|
| | PES/CO 50:50 | | PES/CO 67:33 | |
| | a | b | a | b |
| Constituents g/l | A | B | C | D |
| Product according to Example 3 | | 955 | | |
| Dimethylolmelamine | | 103 | | |
| Silicone oil emulsion (40% strength) | | 35 | | |
| pH value of the bath | | 4.5 | | |
| g of phosphorus per kg of fabric | | 57 | | |
| Liquor uptake, % | | 70 | | |
| Flameproof character | | | | |
| Smouldering time (seconds) | 0 | 0 | 0 | 0 |
| Tear length (cm) | 12 | 12.5 | 13 | 13 |

EXAMPLE 9

Mixed fabrics of polyester-cotton, 50:50 and 67:33, and fabrics of wool and of cotton are padded with the liquors of Table 3 below, dried for 30 minutes at about 80° C and subsequently cured for 5 minutes at 150° C.

The fabrics are rinsed as indicated in Example 7 and rinsed up to 20 times (W: 40° C, PES/CO: 60° C, CO: 95°–100° C).

The individual pieces of fabric are then tested for their flameproof character (DIN 53,906 vertical test, ignition time 6 seconds). The results of this test are also summarised in Table 3.

Table 3

| | Fabrics treated with | | | | | | | | | | | | | | |
|---|---|---|---|---|---|---|---|---|---|---|---|---|---|---|---|
| | PES/CO | | | | | | | | | | | | | W | CO |
| | 50:50 | | | | | | | | | 67:33 | | | | | |
| Constituents, g/l | A | B | C | D | E | F | G | H | I | J | K | L | M | N | O |
| Product according to Example | | | | | | | | | | | | | | | |
| 2 | 1002 | 1002 | | | | | | 1002 | | | | | | 840 | 545 |
| 3 | | | 955 | | | | | | 955 | | | | | | |
| 4 | | | | 620 | 620 | | | | | | 620 | 620 | | | |
| 5 | | | | | | 1009 | | | | | | | 1009 | | |
| 6 | | | | | | | 495 | | | | | | 495 | | |
| Dimethylolmelamine | 103 | 103 | 103 | 103 | 103 | 103 | 103 | 103 | 103 | 103 | 103 | 103 | 103 | 84.5 | 120 |
| Condensation product* | | | | | | | | | | | | | | | |
| Silicone oil emulsion (40% strength) | 35 | 35 | 35 | 35 | 35 | 35 | 35 | 35 | 35 | 35 | 35 | 35 | 35 | 35 | 35 |
| pH value of the bath | 4.5 | 6.5** | 4.5 | 4.5 | 6.5** | 7** | 5.5 | 4.4 | 4.5 | 4.5 | 6.5 | 7** | 5.5 | 4.5 | 4.5 |
| Degree of fixing, % | 71 | 67 | 96 | 84 | 84 | 80 | 73 | 71 | 82 | 65 | 74 | 80 | 65 | 73 | 56 |
| Flameproof character: burning time (seconds) / Tear length (cm) | | | | | | | | | | | | | | | |
| After rinsing | 0/6.5 | 0/7.5 | 0/7.5 | 0/10 | 0/6.5 | 0/4.5 | 2/8 | 0/6.5 | 0/12 | 0/11.5 | 0/13 | 0/7.5 | 3/10 | 2/3.5 | 0/6.5 |
| After 1 wash | 0/7 | 0/6 | 0/8 | 0/7 | 0/9 | 0/8 | 0/8 | 0/7 | 0/10.5 | 3/12 | 3/11.5 | 0/9 | 0/11 | 0/4 | 0/7 |
| After 5 washes | 0/6.5 | 0/7 | 0/8 | 0/7 | 0/8 | 0/9 | 0/8 | 0/6.5 | 0/11 | 0/10 | 0/11 | 0/9 | 0/10 | 6/4.5 | 0/6.5 |
| After 20 washes | 0/6.5 | 0/10 | 0/7 | 3/6 | 0/8 | 4/9.5 | 0/7 | 0/6.5 | 0/12 | 0/10 | 0/11 | 0/9 | 0/10 | 10/8 | 0/8 |

*Condensation product of 1 mol of p-tert.-nonylphenol and 9 mols of ethylene oxide
**Product converted into hydroxy compound

EXAMPLE 10

Fabrics of polyester/cotton (PES/CO), 67:33 and 50:50, are padded with the liquor M according to Example 9 and finished in accordance with the ammonia fixing process:

The padded fabric is dired at up to 80° C (not completely), gassed for 10 minutes with ammonia, then padded in a liquor which contains 300 ml/l of an aqueous 24% strength ammonia solution (liquor ratio 1:30), treated for 10 minutes with a bath which contains 5 g/l of soap and 6 ml/l of $H_2O_2$ (35% strength) kept at 40° C, rinsed and dried.

The fabrics are then washed up to 20 times for 45 minutes at 60° C in a domestic washing machine, using a liquor which contains 4 g/l of a domestic detergent (SNV 198,861 wash). The individual fabric samples are then tested for their flameproof character (DIN 53,906 vertical test; ignition time 6 seconds).

The results are summarised in Table 4 below.

Table 4

| Flameproof character | PES/CO 50:50 | | PES/CO 67:33 | |
|---|---|---|---|---|
| | Burning time seconds | Tear length cm | Burning time seconds | Tear length cm |
| After rinsing | 0 | 6.5 | 0 | 10 |
| After 1 wash | 0 | 8 | 0 | 7 |
| After 5 washes | 0 | 10 | 0 | 8 |
| After 20 washes | 0 | 10.5 | 0 | 8 |

We claim:

1. The water-soluble condensation products produced by the process, comprising the step of reacting and condensing a tetrakis-(hydroxymethyl)-phosphonium salt or hydroxide with a 2,4,6,8,9-pentaazo-bicyclo-nona-2,6-diene of the formula

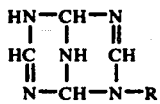

or a salt thereof, wherein R is hydrogen, hydroxyl, lower alkyl, lower alkenyl, cyclohexyl, lower hydroxyalkyl, di(lower alkyl)amino-lower alkyl, phenyl, hydroxyphenyl, N-morpholyl-lower alkyl, pyridyl, pyrimidyl or piperazine-lower alkyl, at a temperature in the range of 40° to 120° C, and in a molar ratio of 1:0.02 to 1:1.

2. The products of claim 1, wherein the starting materials are reacted in the presence of an inert organic solvent.

3. The products of claim 2, wherein the inert organic solvent is an aromatic hydrocarbon.

4. The products of claim 1, wherein the molar ratio is in the range of 1:0.1 to 1:0.5.

5. The products of claim 1, wherein the tetrakis-(hydroxymethyl)-phosphonium salt is a tetrakis-(hydroxymethyl)-phosphonium halide.

6. The products of claim 1, wherein R is hydrogen, methyl, ethyl, or hydroxyalkyl of 1 or 2 carbon atoms.

7. The products of claim 1, wherein the 2,4,6,8,9-pentaazo-bicyclo-[3.3.1]-nona-2,6-diene salt is the salt of an alkylcarboxylic acid of 1 to 3 carbon atoms or the salt of an inorganic acid.

8. The products of claim 1, wherein the starting materials are reacted in the presence of formaldehyde.

9. The products of claim 1, comprising the further step of continuing the reaction at a temperature in the range of 100° to 150° C.

10. The products of claim 1, comprising the further step of treating the resulting condensation product with an alkanol of 1 to 4 carbon atoms to etherify at least part of the free hydroxyl groups thereof.

* * * * *

UNITED STATES PATENT OFFICE
CERTIFICATE OF CORRECTION

PATENT NO. : 4,026,889
DATED : May 31, 1977
INVENTOR(S) : Hermann Nachbur and Arthur Maeder It is certified that error appears in the above-identified patent and that said Letters Patent are hereby corrected as shown below:

On the Cover Page, Item [30] should read:

January 14, 1972   Switzerland . . . . 519/72

Signed and Sealed this sixteenth Day of August 1977

[SEAL]

Attest:

RUTH C. MASON
Attesting Officer

C. MARSHALL DANN
Commissioner of Patents and Trademarks